United States Patent
Sakamoto

(10) Patent No.: US 9,782,190 B2
(45) Date of Patent: Oct. 10, 2017

(54) SURGICAL INSTRUMENT

(71) Applicant: OLYMPUS CORPORATION, Hachioji-shi, Tokyo (JP)

(72) Inventor: Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/402,783

(22) Filed: Jan. 10, 2017

(65) Prior Publication Data

US 2017/0119420 A1   May 4, 2017

Related U.S. Application Data

(63) Continuation of application No. PCT/JP2015/065781, filed on Jun. 1, 2015.

(30) Foreign Application Priority Data

Aug. 4, 2014   (JP) ................. 2014-158914

(51) Int. Cl.
  *A61B 17/068* (2006.01)
  *A61B 17/072* (2006.01)
  *A61B 17/32* (2006.01)

(52) U.S. Cl.
  CPC ............ *A61B 17/32* (2013.01); *A61B 17/072* (2013.01); *A61B 2017/07285* (2013.01)

(58) Field of Classification Search
  CPC ........ A61B 17/072; A61B 2017/07285; A61B 17/068; A61B 2017/07221; A61B 2017/2933; A61B 2017/00323; A61B 2017/2936; A61B 2017/2905; A61B 2017/2937
  USPC ........................................................ 227/180.1
  See application file for complete search history.

(56) References Cited

U.S. PATENT DOCUMENTS

| 5,389,098 | A | 2/1995 | Tsuruta et al. |
| 2008/0169333 | A1 | 7/2008 | Shelton et al. |
| 2008/0308601 | A1 | 12/2008 | Timm et al. |

FOREIGN PATENT DOCUMENTS

| JP | H06-30945 A | 2/1994 |
| JP | H08-289895 A | 11/1996 |
| JP | 2008-220930 A | 9/2008 |
| JP | 2009-034487 A | 2/2009 |

(Continued)

OTHER PUBLICATIONS

Aug. 25, 2015 International Search Report issued in International Patent Application No. PCT/JP2015/065781.

(Continued)

*Primary Examiner* — Michelle Lopez
(74) *Attorney, Agent, or Firm* — Oliff PLC

(57) ABSTRACT

This surgical instrument is provided with: an insertion section; a grasping member provided at a distal end portion of the insertion section and formed in a curved shape; a guide section formed along the curved shape and disposed at the grasping member; a first guided section having a disc shape; a second guided section provided at a proximal side of the guide section closer than the first guided section and having a disc shape; a base to which the first guided member and the second guided member are attached; a blade section fixed to the base and protrudes from the grasping member, the blade section being movably along the curved shape of the grasping member by sliding the first guided member and the second guided member along the guide section.

6 Claims, 12 Drawing Sheets

(56) References Cited

FOREIGN PATENT DOCUMENTS

| | | |
|---|---|---|
| JP | 2010-504815 A | 2/2010 |
| JP | 2011-050744 A | 3/2011 |
| WO | 2008/042045 A2 | 4/2008 |

OTHER PUBLICATIONS

Sep. 6, 2016 Office Action issued in Japanese Patent Application No. 2016-521810.

SURGICAL INSTRUMENT

This application is a continuation application based on PCT Patent Application No. PCT/JP2015/065781, filed Jun. 1, 2015, claiming priority claimed on Japanese Patent Application No. 2014-158914, filed on Aug. 4, 2014, the contents of which are incorporated herein by reference.

BACKGROUND OF THE INVENTION

Field of the Invention

The present invention relates to a surgical instrument.

Background Art

Conventionally, an instrument configured to simultaneously perform suture and dissection of biological tissues is known.

For example, surgical instruments including a cartridge in which a plurality of staples are accommodated, a blade section configured to dissect biological tissues, and a manipulation section for dissecting the tissue using the blade section and shooting staples into the tissue are disclosed in Japanese Unexamined Patent Application, First Publication No. H08-289895, Japanese Unexamined Patent Application, First Publication No. 2011-50744, and Published Japanese Translation No. 2010-504815 of the PCT International Publication.

SUMMARY OF THE INVENTION

A surgical instrument according to a first aspect of the present invention includes: an insertion section configured to be capable of inserting into a body; a grasping member provided at a distal end portion of the insertion section and formed in a curved shape which is bent with respect to an longitudinal axis of the insertion section; a guide section formed along the curved shape and disposed at the grasping member; a first guided section having a disc shape which has an outer circumferential surface slidably contacting with the guide section; a second guided section provided at a proximal side of the guide section closer than the first guided section and having a disc shape which has an outer circumferential surface slidably contacting with the guide section; and a base to which the first guided member and the second guided member are attached; a blade section fixed to the base and protrudes from the grasping member, the blade section being movably along the curved shape of the grasping member by sliding the first guided member and the second guided member along the guide section.

According to a second aspect of the present invention, in the surgical instrument according to the first aspect, the grasping member may have a first jaw and a second jaw, wherein the surgical instrument may further include: a bonding section configured to bond a tissue being grasped by the first and second jaws; and a wire configured to extend from a proximal end portion of the guide section toward a distal end portion of the guide section, to be turned back at the distal end portion of the guide section, to extend toward the proximal end portion of the guide section, and to be coupled with the first guided section, and wherein each of the outer circumferential surface of the first guided section and the outer circumferential surface of the second guided section may have two contacting sections which are capable of contacting with the guide section.

According to a third aspect of the present invention, in the surgical instrument according to the second aspect, the first guided section may be rotatable with respect to the base.

According to a fourth aspect of the present invention, in the surgical instrument according to the third aspect, the second guided section may be rotatable with respect to the base.

According to a fifth aspect of the present invention, in the surgical instrument according to the first aspect, the guide section may include a first guide groove that is a groove formed along the curved shape of the grasping member, and a second guide groove that is formed in a bottom of the first guide groove and has a width narrower than the first guide groove, and the first guided section may abut on an inner surface of the first guide groove and may be guided by the first guide groove, and the second guided section may abut on an inner surface of the second guide groove and may be guided by the first guide groove.

According to a sixth aspect of the present invention, in the surgical instrument according to the first aspect, the first guided section may be rotatable with respect to the blade section.

DETAILED DESCRIPTION OF THE INVENTION

First Embodiment

Figure 1:
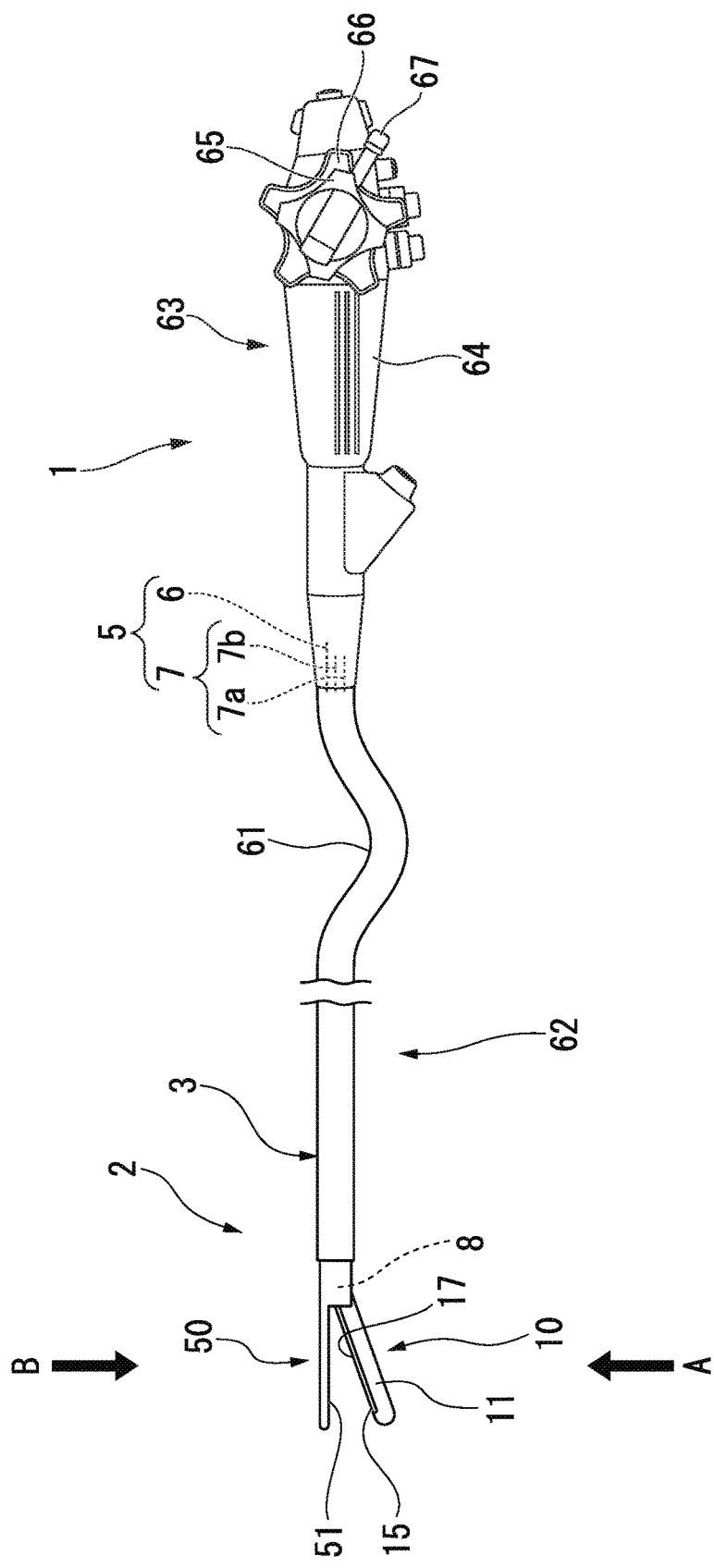
FIG. 1 is an overall view of a surgical instrument according to a first embodiment of the present invention.
Figure 2:
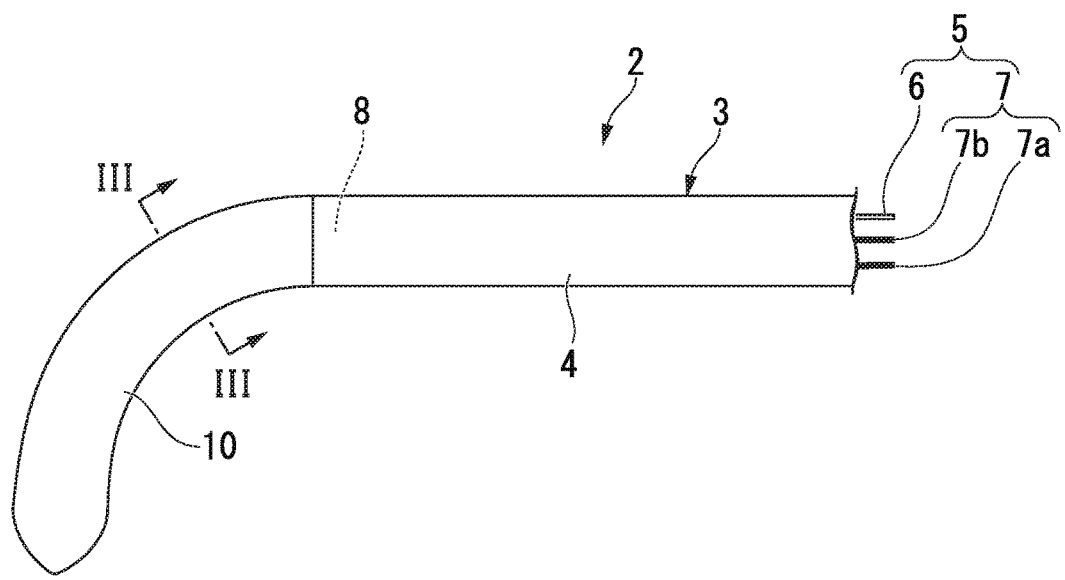
FIG. 2 is a schematic view showing a cartridge section of the surgical instrument according to the first embodiment of the present invention.
Figure 3:
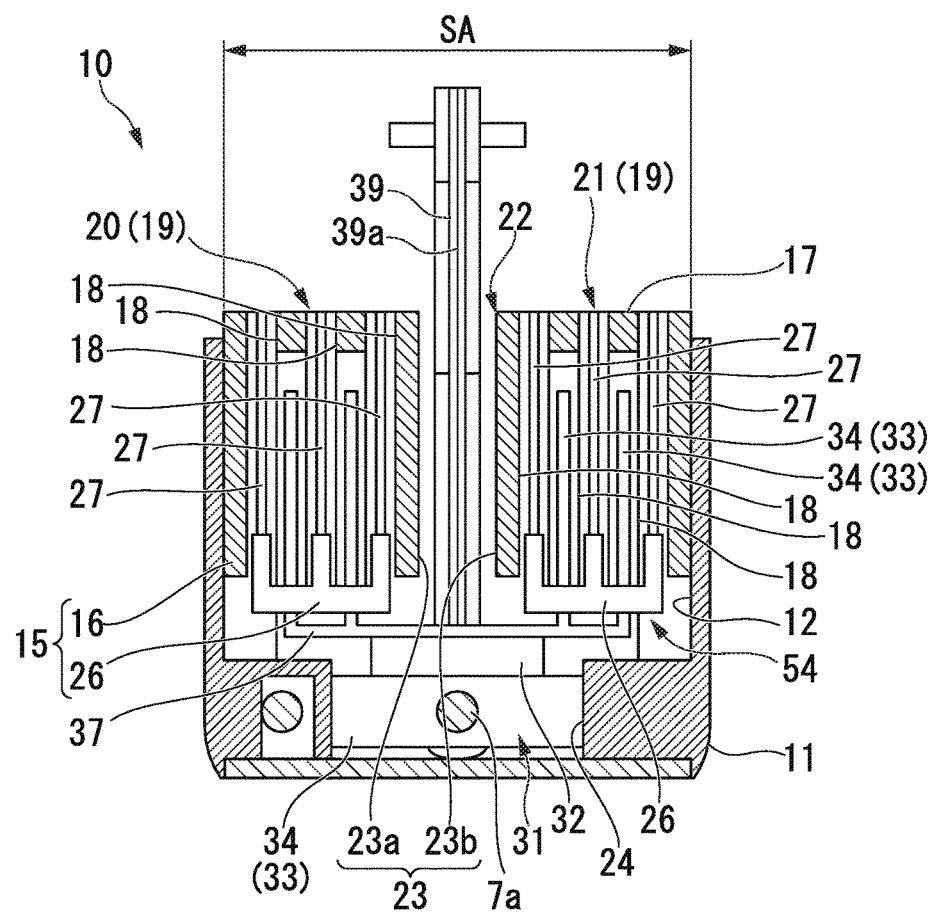
FIG. 3 is a cross-sectional view taken along line III-III of FIG. 2.
Figure 4:
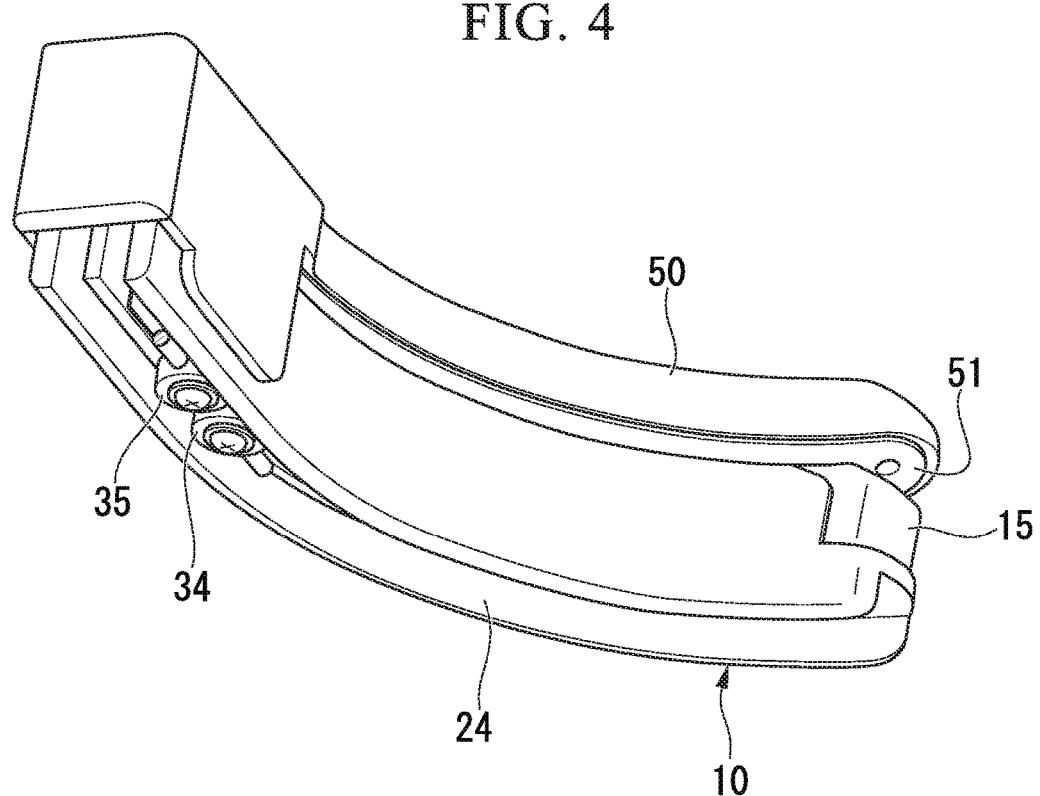
FIG. 4 is a perspective view of a part of the cartridge section of the first embodiment of the present invention.
Figure 5:
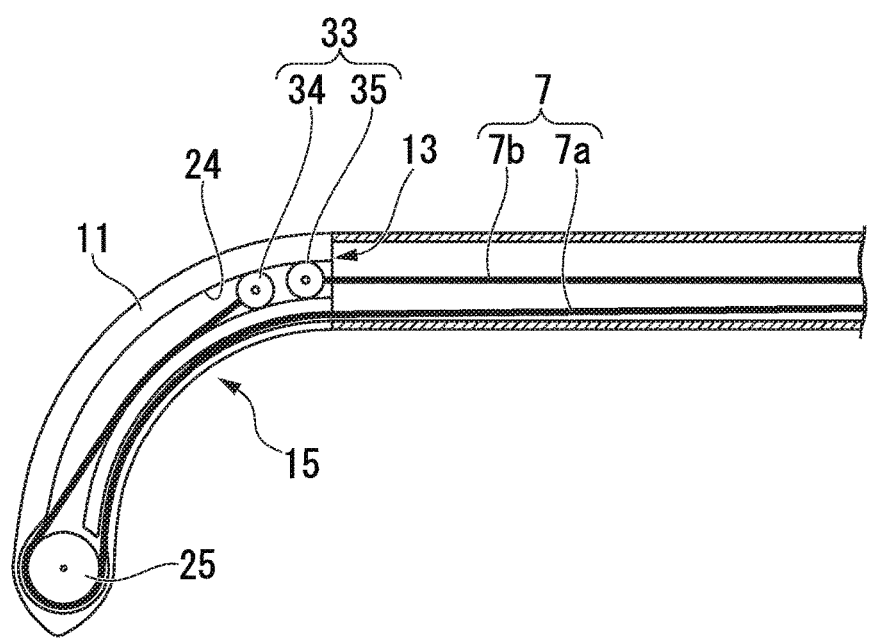
FIG. 5 is a partial cross-sectional view of the cartridge section of the first embodiment of the present invention.
Figure 6:
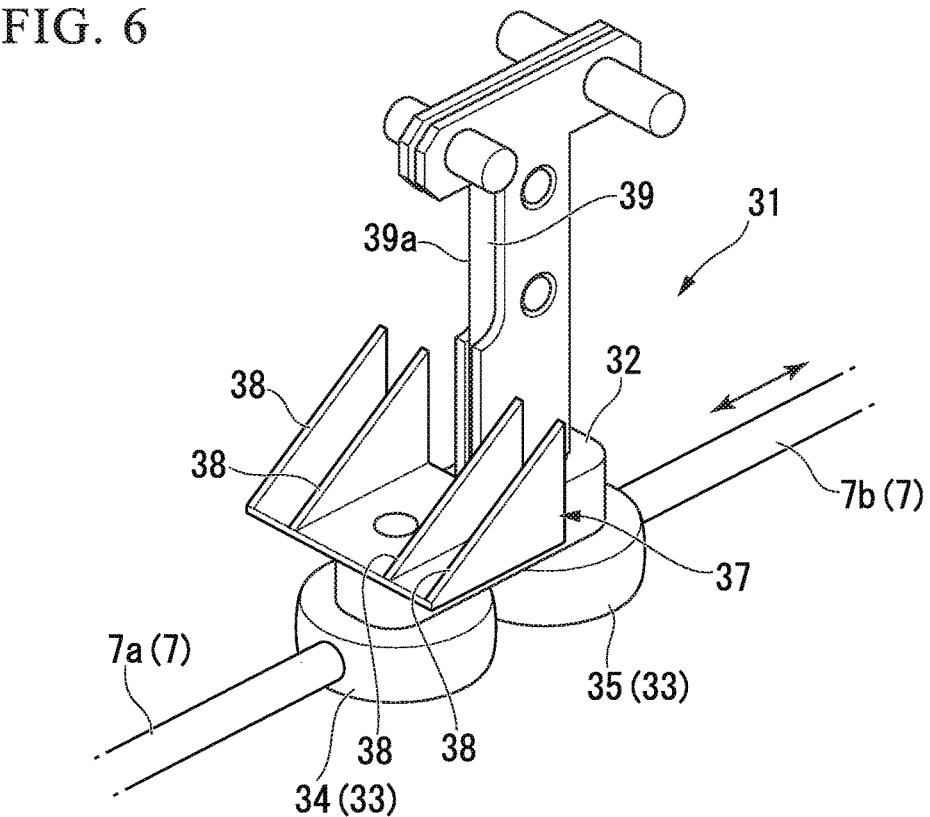
FIG. 6 is a perspective view showing an actuation section installed at the cartridge section of the first embodiment of the present invention.
Figure 7:
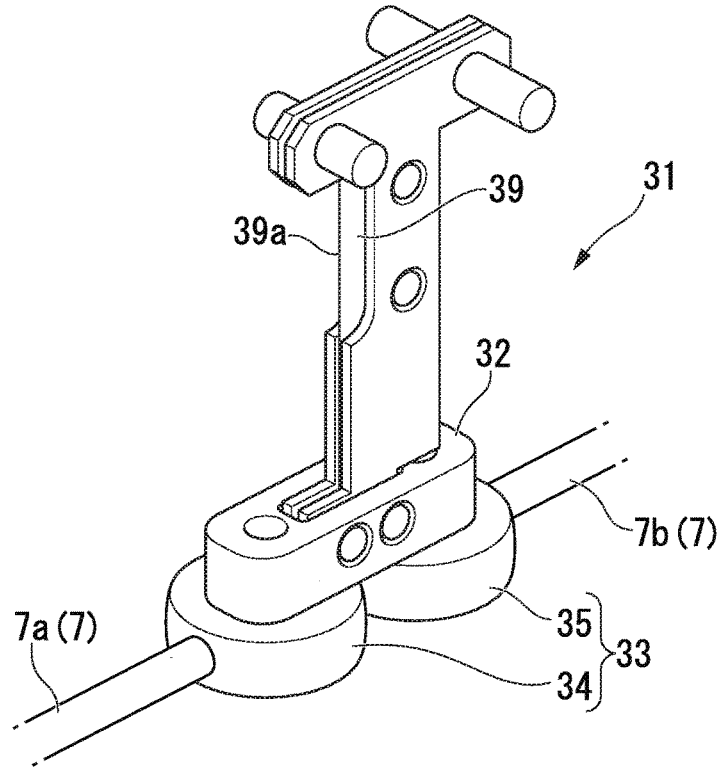
FIG. 7 is a perspective view of the actuation section of the first embodiment of the present invention.
Figure 8:
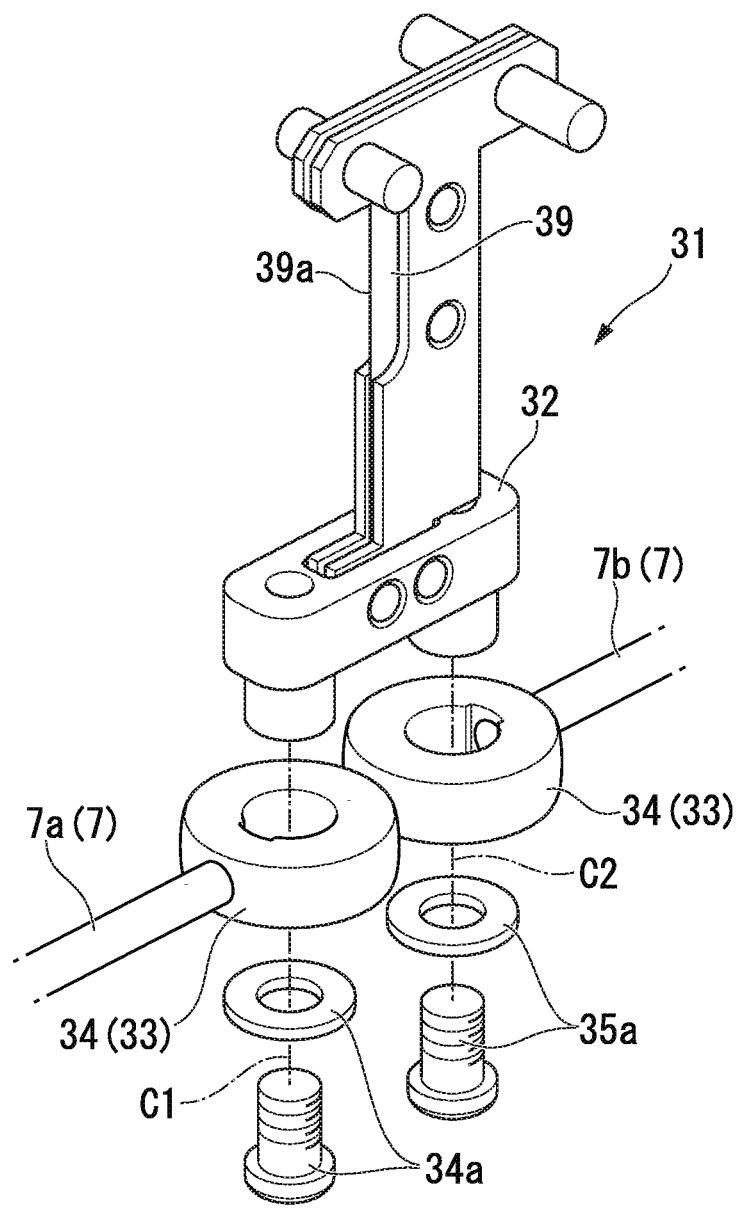
FIG. 8 is an exploded perspective view of the actuation section of the first embodiment of the present invention.
Figure 9:
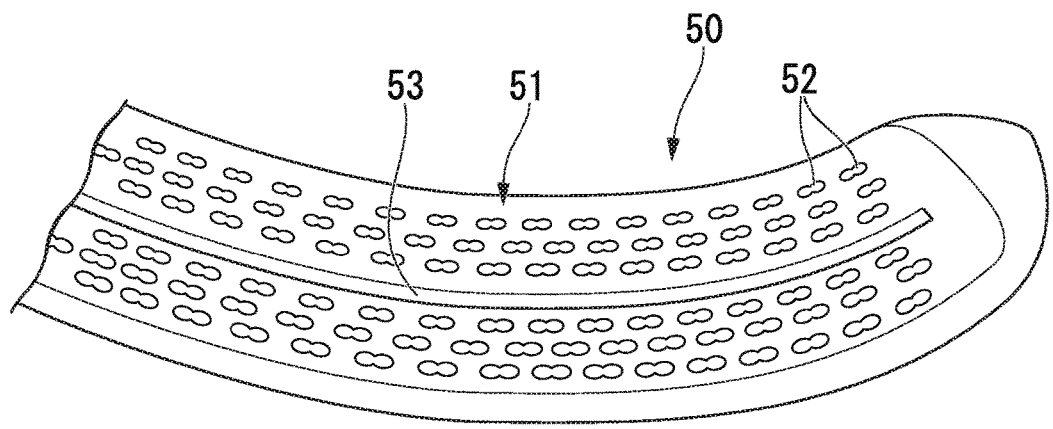
FIG. 9 is a perspective view showing a second jaw of the cartridge section of the first embodiment of the present invention.

A first embodiment of the present invention will be described. FIG. 1 is an overall view showing a surgical instrument 1 according to the embodiment. FIG. 2 is a schematic view showing a cartridge section 2 of the surgical instrument 1 seen in a direction of arrow A shown in FIG. 1. FIG. 3 is a cross-sectional view taken along line of FIG. 2. FIG. 4 is a perspective view showing a part of the cartridge section 2. FIG. 5 is a partial cross-sectional view of the cartridge section 2 seen in a direction of arrow B shown in FIG. 1. FIG. 6 is a perspective view showing an actuation section 31 installed at the cartridge section 2. FIG. 7 is a perspective view of the actuation section 31. FIG. 8 is an exploded perspective view of the actuation section 31. FIG. 9 is a perspective view showing a second jaw 50 of the cartridge section 2.

The surgical instrument 1 according to the embodiment shown in FIG. 1 is a medical tool configured to suture (bond) tissues using staples 27 (see FIG. 12) and to dissect a sutured part.

The surgical instrument 1 is provided with an insertion section 62 which is capable of being inserted into a body, and a manipulation section 63 connected to the insertion section 62.

The insertion section 62 includes a cartridge section 2 into which the staples 27 are charged, and a flexible tube 61 connected to the cartridge section 2.

The cartridge section 2 has a root section 3, an open-close link section 8, a first jaw 10, and a second jaw 50.

As shown in FIGS. 1 and 2, the root section 3 is a substantially tubular area configured to couple the cartridge section 2 with the flexible tube 61.

A proximal end of the root section 3 is fixed to a distal end of the flexible tube 61. A distal end of the root section 3 is connected to the open-close link section 8 and the second jaw 50.

A connecting member 5 operated by manipulation of the manipulation section 63 by the user is inserted into the root section 3. The connecting member 5 has a first connecting member 6 which is provided to open and close the first jaw 10 with respect to the second jaw 50, and a second connecting member (a wire) 7 for operating an actuation section 31 which will be described below.

A proximal end of the first connecting member 6 extends to the manipulation section 63. A distal end of the first connecting member 6 is connected to the open-close link section 8.

As shown in FIG. 5, the second connecting member 7 has a dissection connecting member 7a and a returning connecting member 7b.

The dissection connecting member 7a is wound on a pulley section 25 which will be described below. The dissection connecting member 7a is inserted into a guide section 24 which will be described below. A proximal end of the dissection connecting member 7a extends to the manipulation section 63.

The returning connecting member 7b is capable of being connected to a returning transmission member 73b which will be described below. A distal end of the returning connecting member 7b is coupled with the actuation section 31. In the embodiment, the distal end of the returning connecting member 7b is connected to a proximal end of a base 32 which will be described below. A proximal end of the returning connecting member 7b extends to the manipulation section 63.

The open-close link section 8 is disposed at an inside of a distal portion of the root section 3 shown in FIG. 2. The open-close link section 8 has a link structure configured to convert movement of the first connecting member 6 in a center axis direction of the first connecting member 6 into open-close movement of the first jaw 10.

As shown in FIG. 3, the first jaw 10 has a base section 11, a staple holder 15, staples 27, and the actuation section 31.

As shown in FIG. 3, the base section 11 is a substantially rod-shaped or channel-shaped member having a longitudinal axis and a shape conforming to a curved shape of the first jaw 10.

The base section 11 has a concave section 12 and a communication path 13 to the root section 3. The concave section 12 is capable of accommodating the staple holder 15 and the actuation section 31. The concave section 12 is opened toward a second grasping surface 51 of the second jaw 50. A bottom is formed at the concave section 12 by a cover 14.

As shown in FIG. 5, the communication path 13 to the root section 3 is a passage through which the second connecting member 7 is inserted.

As shown in FIGS. 3 and 4, the staple holder 15 has a holder body 16, a pulley section 25 (see FIG. 5), and a driver 26.

The staple holder 15 has a first grasping surface 17, accommodating sections 18, and a groove section 22. The first grasping surface 17 comes in contact with tissue when tissue is grasped. The staples 27 are accommodated in the accommodating sections 18. The groove section 22 is opened at the first grasping surface 17. The staple holder 15 is attached to the concave section 12 of the base section 11 in a direction in which the first grasping surface 17 is exposed from the base section 11.

The staple holder 15 is detachably attached to the base section 11. For example, after suture by using the staples 27, the staple holder 15 after use is capable of being removed from the base section 11. A suturation by using the surgical instrument 1 according to the embodiment is performed a plurality of times by attaching the staple holder 15 to the base section 11 in place of the used staple holders after suture by using the staples 27.

The first grasping surface 17 is a surface directed toward the second grasping surface 51 (see FIG. 1) of the second jaw 50 in a state in which the holder body 16 is attached to the concave section 12 of the base section 11.

The staples 27 is capable of being accommodated in the accommodating sections 18 in a state in which insertion ends of the staples 27 are directed toward the second grasping surface 51.

As shown in FIG. 3, in the first grasping surface 17, an inner region of an envelope curve that surrounds the plurality of accommodating sections 18 defines a suture area SA in which tissue is sutured by the staples 27. In a state in which the staples 27 are accommodated in the accommodating sections 18, staple arrays 19 (a first staple array 20 and a second staple array 21) are provided in two regions of the holder body 16 divided by the groove section 22.

The first staple array 20 is constituted by of the plurality of staples 27 arranged in an extending direction of the groove section 22. In the embodiment, the first staple array 20 is installed on the first grasping surface 17 in two or more rows at an interval.

The second staple array 21 is constituted by the plurality of staples 27 arranged in the extending direction of the groove section 22. In the embodiment, the second staple array 21 is installed on the first grasping surface 17 in two or more rows at an interval.

Accordingly, the staple array 19 has the plurality of staples 27, which is capable of being shot from the first jaw 10 toward the second jaw 50, around the groove section 22.

As shown in FIG. 3, the groove section 22 is a linear groove in which a blade section 39 (to be described below) of the actuation section 31 is accommodated to be capable of advancing and retracting. In the embodiment, the groove section 22 is formed in a curved shape. The groove section 22 defines a dissection line L (see FIGS. 10 and 13) in the in dissection of tissues.

The groove section 22 has a through-hole 23 and the guide section 24. The through-hole 23 is open to the first grasping surface 17. The guide section 24 is continuous to the through-hole 23 and is formed in the holder body 16.

The through-hole 23 has a first wall surface 23a and a second wall surface 23b that are apart from each other, and a bottom surface that connects the first wall surface 23a and the second wall surface 23b. In the embodiment, a bottom surface of the groove section 22 is constituted by a part of an inner surface of the base section 11. In the embodiment, in an intermediate region of the first jaw 10 in the extending direction of the groove section 22, gaps between the first wall surface 23a and the bottom surface and between the second wall surface 23b and the bottom surface are formed at an intermediate region of the first jaw 10 in the extending direction of the groove section 22 for allowing the actuation section 31 to pass through the intermediate region.

As shown in FIG. 3, the first wall surface 23a has a surface crossing the first grasping surface 17 in the holder body 16. The first wall surface 23a extends from the first grasping surface 17 of the holder body 16 toward a bottom of the concave section 12 of the base section 11. The first wall surface 23a extends in a longitudinal axis direction of the base section 11.

As shown in FIG. 3, the second wall surface 23b is a surface formed in parallel (or nearly parallel) to the first wall surface 23a at a position apart from the first wall surface 23a by a distance at which the blade section 39 of the actuation section 31 is capable of passing therethrough. The second wall surface 23b is a surface crossing the first grasping surface 17 in the holder body 16. The second wall surface 23b extends from the first grasping surface 17 of the holder body 16 toward the bottom of the concave section 12 of the base section 11. The second wall surface 23b extends in the longitudinal axis direction of the base section 11.

As shown in FIGS. 3, 4, and 5, the guide section 24 has a groove shape wider than an interval between the first wall surface 23a and the second wall surface 23b. A first guided section 34 and a second guided section 35 which constitute a pair of guided sections 33 provided for the actuation section 31 is capable of coming in contact with the guide section 24.

The dissection connecting member 7a is inserted into the guide section 24. In the guide section 24, the dissection connecting member 7a extends from a proximal end portion toward a distal end portion of the guide section 24 along the guide section 24, turns at the pulley section 25 of the distal end portion of the guide section 24 to extend to the proximal end portion of the guide section 24, and is coupled with the actuation section 31. In the embodiment, a distal end of the dissection connecting member 7a is connected to a distal end of the base 32, which will be described below.

The dissection connecting member 7a is wound on the pulley section 25 shown in FIG. 5. The pulley section 25 is rotatably coupled with the base section 11.

The driver 26 shown in FIG. 3 is disposed inside the accommodating sections 18. The driver 26 can be displaced in the accommodating section 18 by a cam section 37 of the actuation section 31. That is, when the driver 26 is moved toward an opening of the first grasping surface 17 side of the accommodating sections 18 by the cam section 37 (see FIG. 6), the driver 26 pushes a connecting section 30 of each of the staples 27 (see FIG. 12) toward the opening of the first grasping surface 17 side to push out the staples 27 from the accommodating sections 18.

Each of the staples 27 has a pair of leg sections 28 and 29 (see FIG. 13) having insertion ends inserted into the tissue, and the connecting section 30 that couples the pair of leg sections 28 and 29. Each of the staples 27 is formed in a U shape (a U shape in which all angles are right angles) by bending deformable strands having high biocompatibility. A known structure may be selected and employed as the shape of the staple 27.

The actuation section 31 shown in FIGS. 6, 7, and 8 is disposed inside the base section 11. The actuation section 31 is configured to move the driver 26 to push out the staples 27 from the accommodating section 18 and also dissect the tissues after the staples 27 are pushed out.

As shown in FIGS. 6, 7, and 8, the actuation section 31 has the base 32, the pair of guided sections 33, the cam section 37, and the blade section 39.

The base 32 is connected to a distal end of the second connecting member 7 of the connecting member 5. The base 32 is capable of moving by movement of the second connecting member 7 in a direction of the central axis thereof.

The pair of guided sections 33, the cam section 37, and the blade section 39 are attached to the base 32.

The pair of guided sections 33 are members engaged with the guide section 24. In the embodiment, each of the pair of guided sections 33 are capable of coming into contact with the guide section 24.

The pair of guided sections 33 have the first guided section 34 disposed at a distal side of the base 32, and the second guided section 35 disposed at a proximal side of the base 32.

The first guided section 34 is a member that has a disk shape having a centerline C1 in a thickness direction of the base 32 and is coupled with the base 32. As shown in FIG. 8, the first guided section 34 is mounted on the base 32 by a screw 34a to be rotatable about the centerline C1 of the first guided section 34. The distal end of the dissection connecting member 7a is fixed to the first guided section 34.

The second guided section 35 is a member that has a disk shape having a centerline C2 in the thickness direction of the base 32 and is coupled with the base 32. As shown in FIG.

8, the second guided section 35 is mounted on the base 32 by a screw 35a to be rotatable about the centerline C2 of the second guided section 35. The distal end of the returning connecting member 7b is fixed to the second guided section 35.

As shown in FIGS. 3 and 6, the cam section 37 has inclined surfaces 38 inclined with respect to the longitudinal axis of the base section 11. The inclined surface 38 of the cam section 37 comes into contact with the driver 26 to move the driver 26 when the cam section 37 is moved in the longitudinal axis direction of the base section 11. The moving direction of the cam section 37 is an extending direction of the groove section 22.

As shown in FIG. 6, the blade section 39 is disposed at a proximal side relative to the cam section 37. The blade section 39 has a sharp blade edge 39a, which is capable of dissecting biological tissues, at a distal side. As shown in FIG. 3, the blade edge 39a of the blade section 39 is located in the middle between the first guided section 34 and the second guided section 35. The blade section 39 is disposed in the groove section 22 to protrude from the first grasping surface 17 toward the second jaw 50 side. An amount of protrusion of the blade section 39 from the first grasping surface 17 is such an amount of protrusion that the blade section 39 is not caught by the second grasping surface 51 of the second jaw 50 when the first jaw 10 and the second jaw 50 are in a closed state.

As shown in FIG. 9, the second jaw 50 has the second grasping surface 51 in which a plurality of molded pockets 52 is formed.

The second grasping surface 51 is a surface directed toward the first grasping surface 17 of the first jaw 10. When the first jaw 10 is closed with respect to the second jaw 50, a distance between the first grasping surface 17 of the first jaw 10 and the second grasping surface 51 of the second jaw 50 is previously set depending on thicknesses of tissues as a suture target. The distance between the first grasping surface 17 of the first jaw 10 and the second grasping surface 51 of the second jaw 50 is set to a distance at which the tissues to be sutured after the suture using the staples 27 are adhered and excessive debridement of the tissues to be sutured is hard to occur.

The molded pockets 52 and a relief groove 53 are formed in the second grasping surface 51. The relief groove 53 is formed such that a protruding end of the blade section 39 is capable of entering and the relief groove 53 is formed to be long in the longitudinal axis direction of the second jaw 50.

Figure 13:
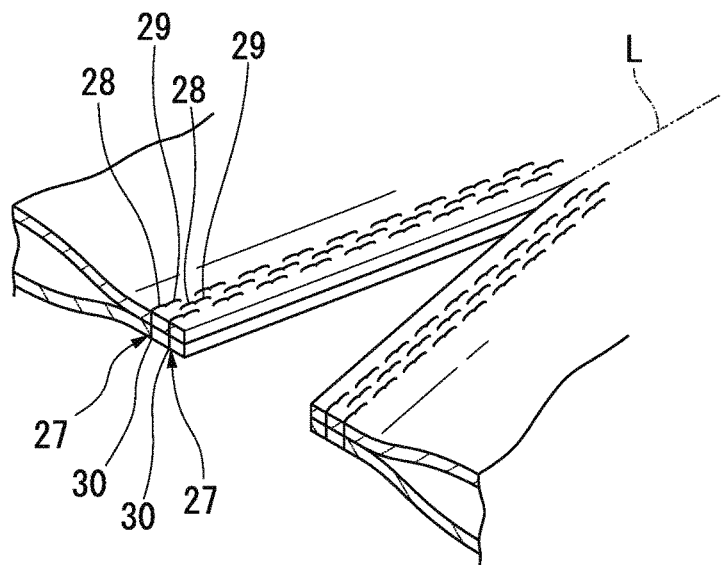
FIG. 13 is a view showing an action of the surgical instrument according to the first embodiment of the present invention.

Each of the molded pockets 52 shown in FIG. 9 has an inclined surface or a curved surface that is configured to guide the leg sections 28 and 29 in order to plastically deform the leg sections 28 and 29 of the staples 27 to form a shape in which the tissues are sutured as shown in FIG. 13.

As shown in FIG. 9, the relief groove 53 is formed to be recessed from the second grasping surface 51 in order to ensure the dissection of the tissues caused by the blade section 39. When the protruding end of the blade section 39 enters the relief groove 53, the first jaw 10 and the second jaw 50 are maintained in a closed state.

In the embodiment, a suture (bonding) section 54 (see FIG. 3) that sutures (bonds) tissues is constituted by the staple holder 15, the staples 27, the cam section 37, and the second jaw 50.

As shown in FIG. 1, the flexible tube 61 is a tubular elongated member. The connecting member 5 (the first connecting member 6, the dissection connecting member 7a, and the returning connecting member 7b) is inserted through the flexible tube 61.

The proximal end of the root section 3 of the cartridge section 2 is fixed to the distal end of the flexible tube 61. A proximal end of the flexible tube 61 is fixed to the manipulation section 63.

A pipe line configured to guide a known observation apparatus (for example, an endoscope) for observing a suture area from the manipulation section 63 toward the cartridge section 2 side may be installed at the flexible tube 61.

The manipulation section 63 is provided at the proximal end of the flexible tube 61. The manipulation section 63 is provided to allow a user to perform manipulation of opening and closing the first jaw 10 and the second jaw 50, stapling the staples 27 to tissues, and further dissecting tissues. The manipulation section 63 has a substantially a rod shape such that an operator is capable of gripping the manipulation section 63 with his or her hand.

The manipulation section 63 has a housing 64, a curved knob 65, an open-close knob 66, a lever 67, and a transmission mechanism (not shown). The housing 64 has a substantially rod shape and is formed a space inside of the housing. The curved knob 65 is provided to bend the flexible tube 61. The open-close knob 66 and the lever 67 are disposed to be exposed to the outside of the housing 64 to operate the connecting member 5. The transmission mechanism is connected to the connecting member 5 in the housing 64.

The curved knob 65 is a member configured to bend the flexible tube 61 by pulling an angle wire (not shown) extending from the distal end of the flexible tube 61 to the manipulation section 63. The curved knob 65 is rotatable with respect to the housing 64 of the manipulation section 63, and is capable of being fixed not to be rotated with respect to the housing 64 at an arbitrary position.

The open-close knob 66 is a member configured to advance and retract the first connecting member 6 in a centerline direction thereof. The open-close knob 66 is rotatable with respect to the housing 64 of the manipulation section 63, and is capable of being fixed not to be rotated with respect to the housing 64 at an arbitrary position.

As an operator operates the open-close knob 66, the transmission mechanism (not shown) transmits an amount of force for manipulating the open-close knob 66 to the first connecting member 6 as an amount of force to advance and retract the first connecting member 6 backward or forward in the centerline direction.

The lever 67 is a member configured to advance and retract the second connecting member 7 in the centerline direction. The lever 67 is swingable with respect to the housing 64 of the manipulation section 63, and is capable of being fixed not to be swung with respect to the housing 64 at an arbitrary position.

As the operator manipulates the lever 67, the transmission mechanism (not shown) transmits an amount of force for manipulating the lever 67 to the second connecting member 7 as an amount of force to advance and retract the second connecting member 7 in the centerline direction. In the embodiment, the dissection connecting member 7a is pulled to the proximal side, when the lever 67 is swung in one predetermined direction, and the returning connecting member 7b is pulled to the proximal side when the lever 67 is swung in a direction opposite to the one predetermined direction.

The dissection connecting member 7a and the returning connecting member 7b are connected to each other via the actuation section 31 in the cartridge section 2. For this reason, the returning connecting member 7b is moved to the distal side when the dissection connecting member 7a is pulled to the proximal side by the lever 67, and the dissection connecting member 7a is moved to the distal side when the returning connecting member 7b is pulled to the proximal side by the lever 67.

Next, an action of the surgical instrument according to the embodiment will be described. FIGS. 10 to 13 are views showing the action of the surgical instrument 1 according to the embodiment.

As shown in FIG. 3, the surgical instrument 1 is prepared in a state in which the staples 27 are accommodated in the accommodating section 18 and the cam section 37 and the blade section 39 are disposed in the vicinity of the proximal end of the base section 11. As shown in FIG. 5, at this time, the pair of guided sections 33 of the actuation sections 31 are disposed in the vicinity of the proximal ends of the guide section 24.

The surgical instrument 1 is guided to a treatment target area, for example, a natural opening of a patient such as the mouth of the patient, or a small incised portion formed in the abdominal wall of the patient.

Figure 10:
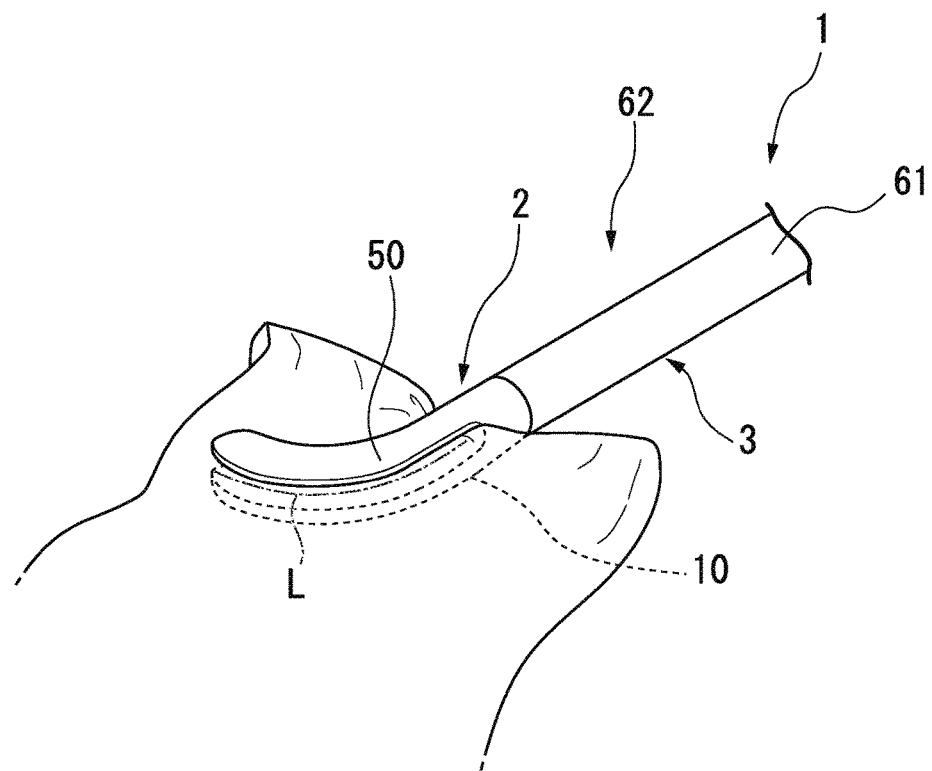
FIG. 10 is a view showing an action of the surgical instrument according to the first embodiment of the present invention.
Figure 11:
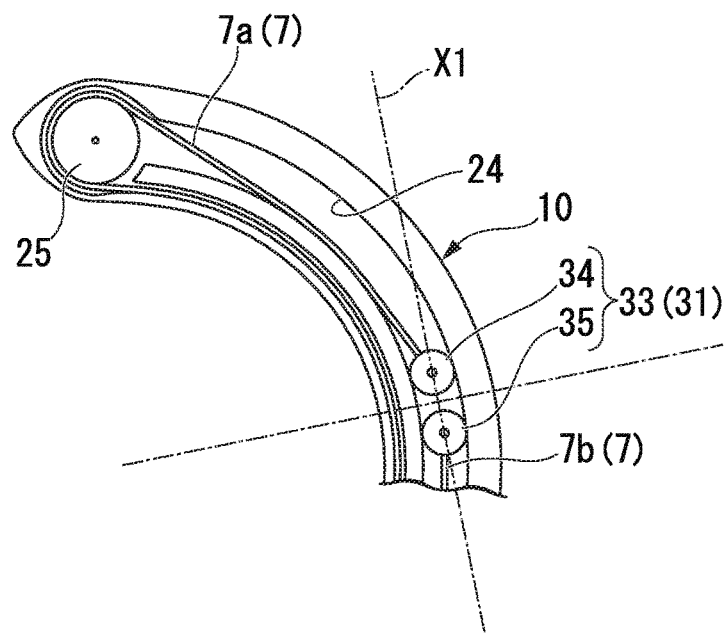
FIG. 11 is a view showing an action of the surgical instrument according to the first embodiment of the present invention.

As shown in FIG. 10, the first jaw 10 and the second jaw 50, which are provided at the distal end portion of the insertion section 62 of the surgical instrument 1, grasp the tissue serving as the dissection target in accordance with a manipulation of the open-close knob 66 (see FIG. 1) of the manipulation section 63 under the observation of a laparoscope (not shown).

As shown in FIG. 10, as the first jaw 10 and the second jaw 50 grasp the tissue serving as the dissection target, the dissection line L is defined with respect to the dissection target tissues. As a user fixes the open-close knob 66 shown in FIG. 1 to the housing 64, a position of the first jaw 10 with respect to the second jaw 50 is fixed in the state in which the first jaw 10 and the second jaw 50 grasp the tissues as shown in FIG. 10.

The user operates the lever 67 to move the dissection connecting member 7a to the proximal side after fixing the open-close knob 66 shown in FIG. 1 to the housing 64. The dissection connecting member 7a moved to the proximal side moves the actuation section 31 to the distal side as a pulling direction is reversed by the pulley section 25 The actuation section 31 moves both of the cam section 37 and the blade section 39 shown in FIGS. 3 and 6 to the distal side. The driver 26 shown in FIG. 3 is pushed up by the inclined surface 38 of the cam section 37 which is moved to the distal side. The driver 26 shown in FIG. 3 pushes out the staples 27 from the accommodating section 18 such that insertion ends of the staples 27 pierce into the tissue as the driver 26 is pushed up to the inclined surface 38 of the actuation section 31.

Further, when the staples 27 are pushed out from the accommodating sections 18, the leg sections 28 and 29 of the staples 27 abut the molded pockets 52 (see FIG. 9). The molded pockets 52 deform the leg sections 28 and 29 of the staples 27 into a predetermined shape for suturing the tissue as shown in FIG. 13. The staples 27 are sequentially shot from the accommodating sections 18 from a proximal side toward a distal side of the first jaw 10 in accordance with a movement of the cam section 37. In this way, the suture section (the bonding section) 54 shown in FIG. 3 sutures (bonds) the tissues grasped by the first jaw 10 and the second jaw 50 via the staples 27.

The blade section 39 (see FIG. 6) disposed at a proximal side of the cam section 37 moves along the groove section 22 between the first staple array 20 and the second staple array 21 serving as the dissection line L (see FIGS. 10 and 13). At this time, the blade section 39 comes into contact with neither of the first and second wall surfaces 23a and 23b of the groove section 22, the guide section 24 comes into contact with the first guided section 34 and the second guided section 35 and guides the first guided section 34 and the second guided section 35, and thereby a direction of the blade section 39 is regulated by a tangential direction X1 (see FIG. 11) of the groove section 22. That is, since the blade edge 39a of the blade section 39 is located in the middle between the first guided section 34 and the second guided section 35, a direction of the blade edge 39a is regulated by the tangential direction of the groove section 22. Since the blade edge 39a is located at a position separated from either of the first wall surface 23a and the second wall surface 23b to the maximum, the blade edge 39a is hard to bite into the first wall surface 23a or the second wall surface 23b.

Figure 12:
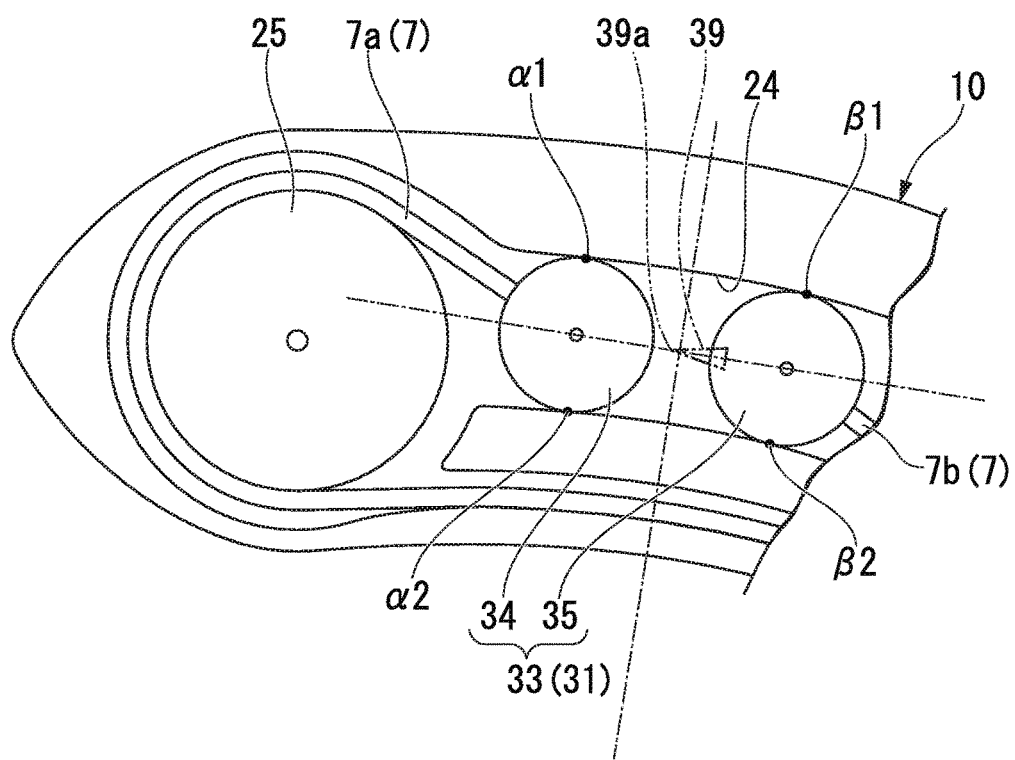
FIG. 12 is a view showing an action of the surgical instrument according to the first embodiment of the present invention.

The first guided section 34 in the pair of guided sections 33 is supported by the guide section 24 at two opposite points ($\alpha 1$ and $\alpha 2$ shown in FIG. 12), and the second guided section 35 in the pair of guided sections 33 is supported by the guide section 24 at two opposite points ($\beta 1$ and $\beta 2$ shown in FIG. 12). That is, the pair of guided sections 33 are supported by the guide section 24 at four points different from one another. For this reason, a variation in the direction of the blade section 39 is small, and an unsteadily movement of the blade section 39 due to the movement of the blade section 39 hardly occur.

The tissue is sequentially dissected by the blade section 39 from an area sutured by the staples 27. The blade section 39 dissects the tissue in the suture area SA, in the tissue grasped by the first jaw 10 and the second jaw 50.

As shown in FIG. 12, when the actuation section 31 reaches the farthest distal end of the first jaw 10, the first guided section 34 is turned such that the dissection connecting member 7a located between the first guided section 34 and the pulley section 25 becomes a linear shape in a tangential direction of the pulley section 25. Thereby, it is difficult for bending stress to be applied to the dissection connecting member 7a, and the dissection connecting member 7a is hardly damaged even if the dissection connecting member 7a is pulled with a strong force.

As the second guided section 35 is also capable of being turned like the first guided section 34, the returning connecting member 7b is hardly damaged even if the returning connecting member 7b is pulled with a strong force.

After completion of suture by the staples 27 and dissection by the blade section 39, a user operates and releases the open-close knob 66 to open the first jaw 10 relative to the second jaw 50. Accordingly, grasping of the tissue by the first jaw 10 and the second jaw 50 is released.

According to necessity, the actuation section 31 is capable of moving to the proximal end side of the groove section 22 by which the returning connecting member 7b is moved to the proximal side by operating the lever 67. When the actuation section 31 is positioned at the proximal end portion of the groove section 22, the empty staple holder 15 after shooting of the staples 27 is capable of replacing with a new staple holder 15.

When treatment is performed a plurality of times by using the surgical instrument 1 according to the embodiment, suture and dissection are capable of continuously performing by replacing the staple holder 15 with a new one after shooting the staples 27 to continue suture and dissection.

As described above, according to the surgical instrument 1 related to the embodiment, since the blade section 39 is guided by the guide section 24 while being held not to be in contact with the groove section 22, the movement of the blade section 39 is smooth in the process of dissecting the tissues.

Second Embodiment

Figure 14:
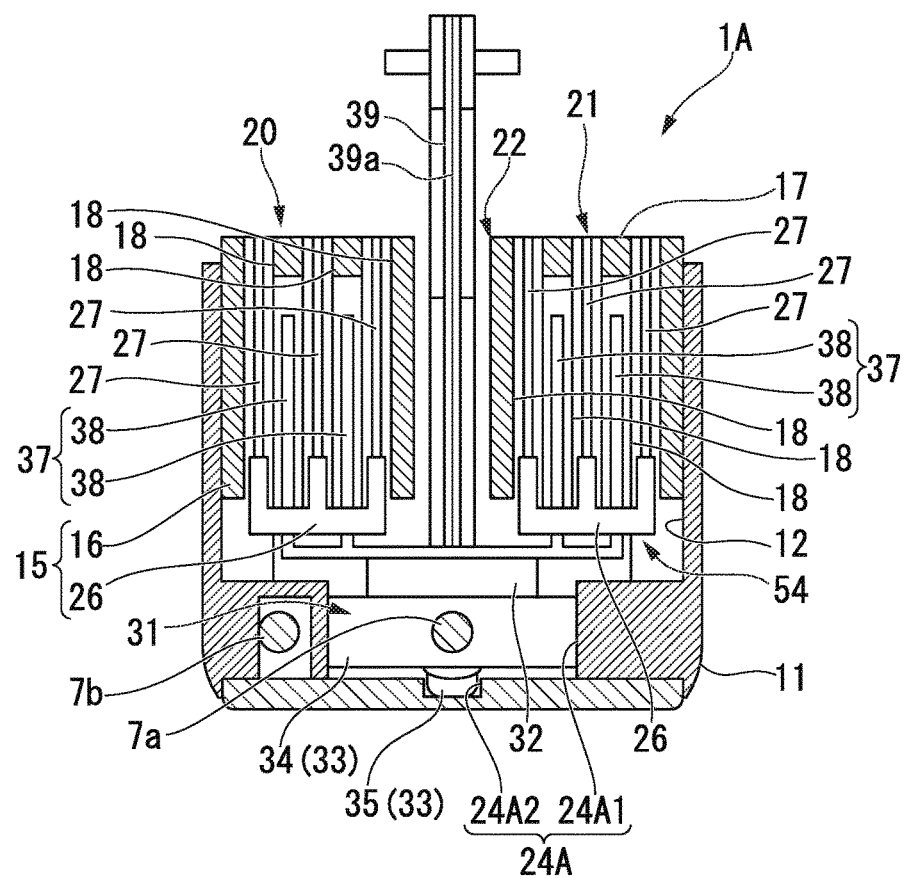
FIG. 14 is a cross-sectional view showing a cartridge section of a surgical instrument according to a second embodiment of the present invention, and showing the same cross-section taken along line of FIG. 2.
Figure 15:
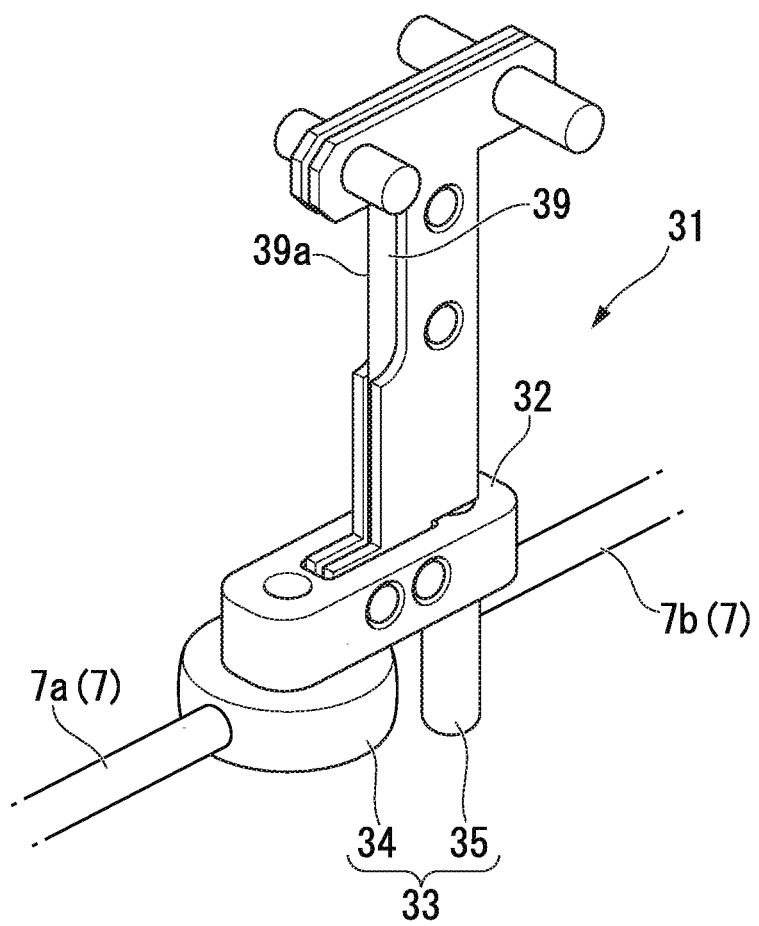
FIG. 15 is a perspective view showing an actuation section installed at the cartridge section of the second embodiment of the present invention.
Figure 16:
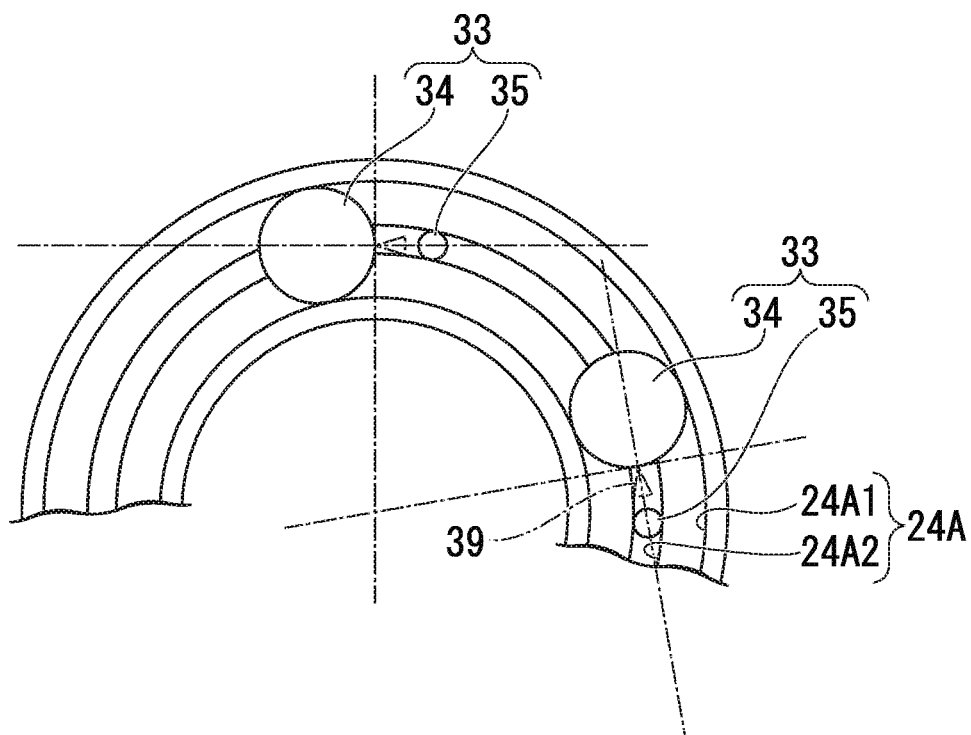
FIG. 16 is a view showing an operation of the surgical instrument according to the second embodiment of the present invention.

Next, a second embodiment of the present invention will be described. In the embodiments described below, the same components as the components in description of the first embodiment are designated by the same reference numerals as in the first embodiment, and overlapping description will be omitted. FIG. 14 is a cross-sectional view showing a cartridge section of a surgical instrument 1A according to the embodiment, and shows a cross-section taken along line III-III of FIG. 2. FIG. 15 is a perspective view showing an actuation section 31 provided for the cartridge section of the embodiment. FIG. 16 is a view showing an operation of the surgical instrument 1A according to the embodiment.

The surgical instrument 1A according to the embodiment is different from that of the first embodiment in that it has a guide section 24A in place of the guide section 24 described in the first embodiment and in that a pair of guided sections 33 are guided by the guide section 24A. To be specific, in the embodiment, the guide section 24A has a first guide groove 24A1 and a second guide groove 24A2. The embodiment is different from the first embodiment in that a first guided section 34 of the pair of guided sections 33 is guided by the first guide groove 24A1 and in that a second guided section 35 of the pair of guided sections 33 is guided by the second guide groove 24A2, which are different from the first embodiment.

The first guide groove 24A1 is formed along a curved shape of the groove section 22, and has a groove shape having a width within which the first guided section 34 is insertable.

The second guide groove 24A2 is formed in a bottom of the first guide groove 24A1, is formed along the curved shape of the groove section 22, and has a groove shape having a narrower width than the first guide groove 24A1. The second guide groove 24A2 is a groove having a width within which the second guided section 35 is insertable.

The first guided section 34 abuts on an inner surface of the first guide groove 24A1, and is guided by the first guide groove 24A1.

In the embodiment, the second guided section 35 has a rod shape that is thinner than the first guided section 34. The second guided section 35 abuts on an inner surface of the second guide groove 24A2, and is guided by the first guide groove 24A1.

In the embodiment, the guidance of the first guided section 34 caused by the first guide groove 24A1 and the guidance of the second guided section 35 caused by the second guide groove 24A2 are independent of each other. That is, a curvilinear shape of the first guide groove 24A1 and a curvilinear shape of the second guide groove 24A2 have shapes different from each other (for example, shapes that have different radii of curvature and are parallel to each other), and thereby a direction of a blade section 39 can be set to a suitable direction.

For example, as shown in FIG. 16, when the second guide groove 24A2 is present in the middle of the first guide groove 24A1, the blade section 39 disposed in the middle between the first guided section 34 and the second guided section 35 is regulated to have the same direction as in the first embodiment.

When the guide section 24A is formed such that a central axis of the second guide groove 24A2 is located at an outer circumference side relative to a central axis of the first guide groove 24A1, the blade section 39 directs in a direction in which the blade section 39 easily bites into the inside compared to when the central axis of the first guide groove 24A1 coincides with the central axis of the second guide groove 24A2. Conversely, when the guide section 24A is formed such that the central axis of the second guide groove 24A2 is located at an inner circumference side relative to the central axis of the first guide groove 24A1, the blade section 39 directs in a direction in which the blade section 39 easily bites into the outside compared to when the central axis of the first guide groove 24A1 coincides with the central axis of the second guide groove 24A2.

Figure 17:
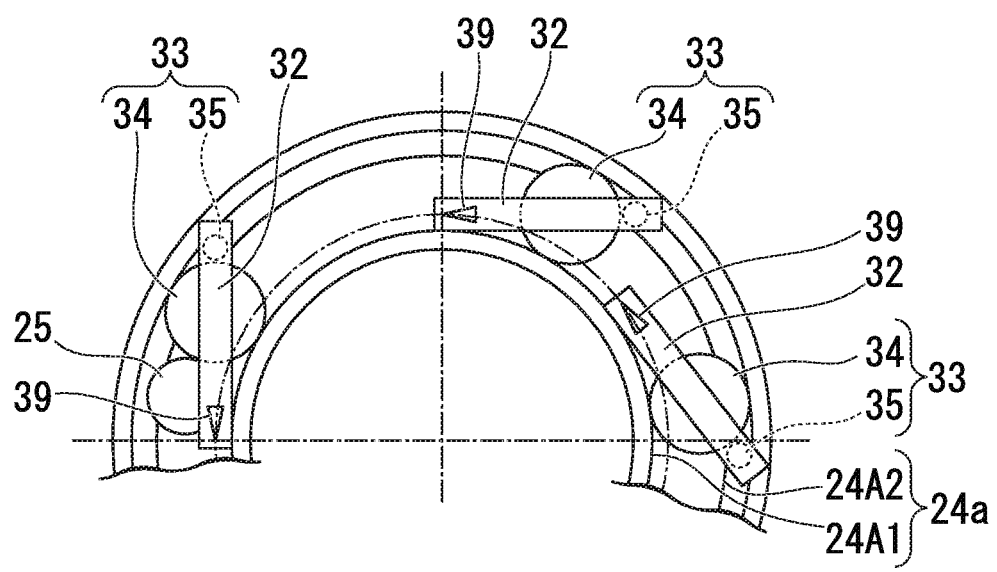
FIG. 17 is a view showing a modified example of the second embodiment of the present invention.

As shown in FIG. 17, in a case that the blade section 39 described in the first embodiment is located closer to the first guided section 34, namely closer to the distal side of the actuation section 31 compared to the case of the first embodiment, the guide section 24A may be formed such that the central axis of the second guide groove 24A2 is located at the outer circumference side relative to the central axis of the first guide groove 24A1 in order to set a direction of the blade section 39 to a tangential direction of the groove section 22.

In the embodiment, a degree of freedom of the disposition of the blade section 39 with respect to the pair of guided sections 33 can be made greater, compared to the first embodiment. In the embodiment, the blade section 39 can be disposed at a distal portion of the actuation section 31, and the blade section 39 can be displaced up to a position closer to a distal end of the first jaw 10. For this reason, in the embodiment, a dissection length by a single dissecting operation is capable of being longer than that of the first embodiment.

Third Embodiment

Figure 18:
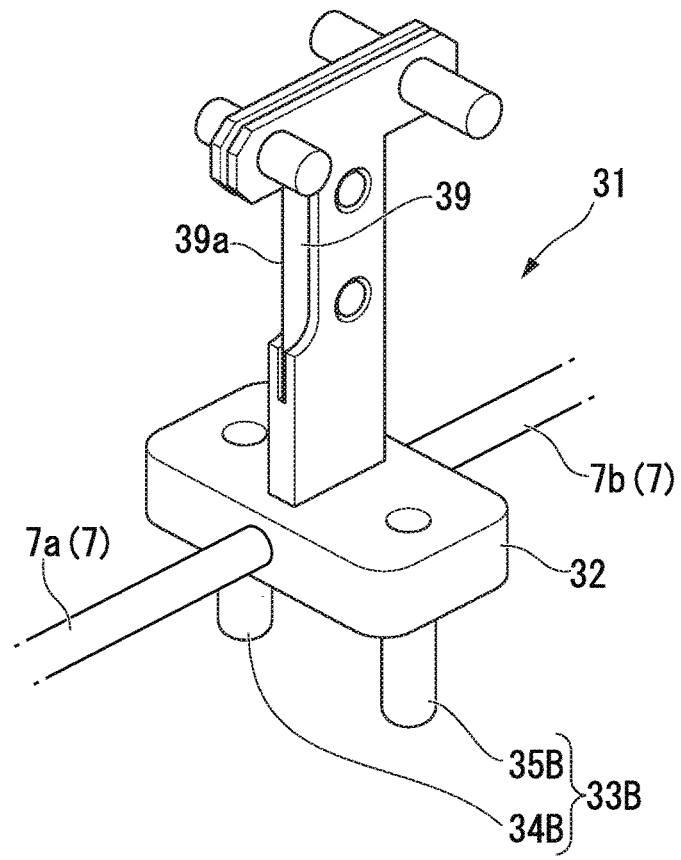
FIG. 18 is a perspective view showing an actuation section installed at the cartridge section of a surgical instrument according to a third embodiment of the present invention.
Figure 19:
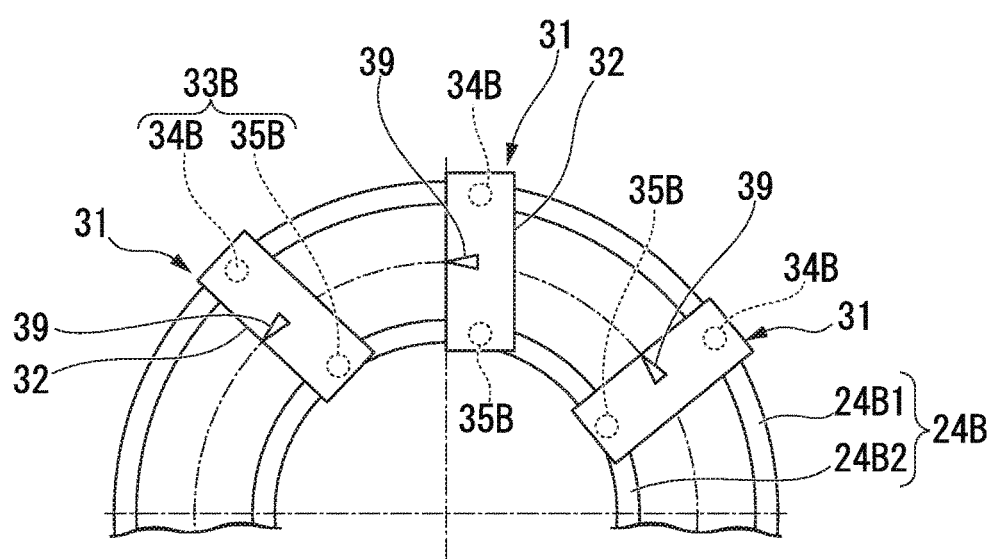
FIG. 19 is a view showing an action of the surgical instrument according to the third embodiment of the present invention.

Next, a third embodiment of the present invention will be described. FIG. 18 is a perspective view showing an actuation section 31 installed at a cartridge section of a surgical instrument according to the embodiment. FIG. 19 is a view showing an action of the surgical instrument according to the embodiment.

The surgical instrument according to the embodiment has a difference in the guide section 24 and the guided sections 33 described in the first embodiment. The guide section 24B of the embodiment has a first guide groove 24B 1 and a second guide groove 24B2 that are parallel to each other. The pair of guided sections 33B of the embodiment has a first guided section 34B and a second guided section 35B that are parallel (includes nearly parallel) to each other.

The first guide groove 24B1 and the second guide groove 24B2 are separated from each other, and may have curvilinear shapes different from each other in order to adjust a direction of a blade section 39 like the second embodiment.

In the embodiment, the first guide groove 24B1 and the second guide groove 24B2 have arcuate shapes that form parts of concentric circles whose radii are different from each other.

The first guided section 34B abuts on an inner surface of the first guide groove 24B1, and is guided by the first guide groove 24B1.

The second guided section 35B abuts on an inner surface of the second guide groove 24B2, and is guided by the second guide groove 24B2.

In the embodiment, as shown in FIG. 18, a dissection connecting member 7a is coupled to a distal side of a base 32 of the actuation section 31 relative to the first guided section 34B and the second guided section 35B. Moreover, the dissection connecting member 7a is coupled to the distal side of the base 32 relative to the blade section 39.

Also in the embodiment, the same effects as the first embodiment are exerted. In the embodiment, when viewed in a direction in which a groove section 22 extends, a length of the actuation section 31 is capable of being shorter, compared to the first embodiment.

Figure 20:
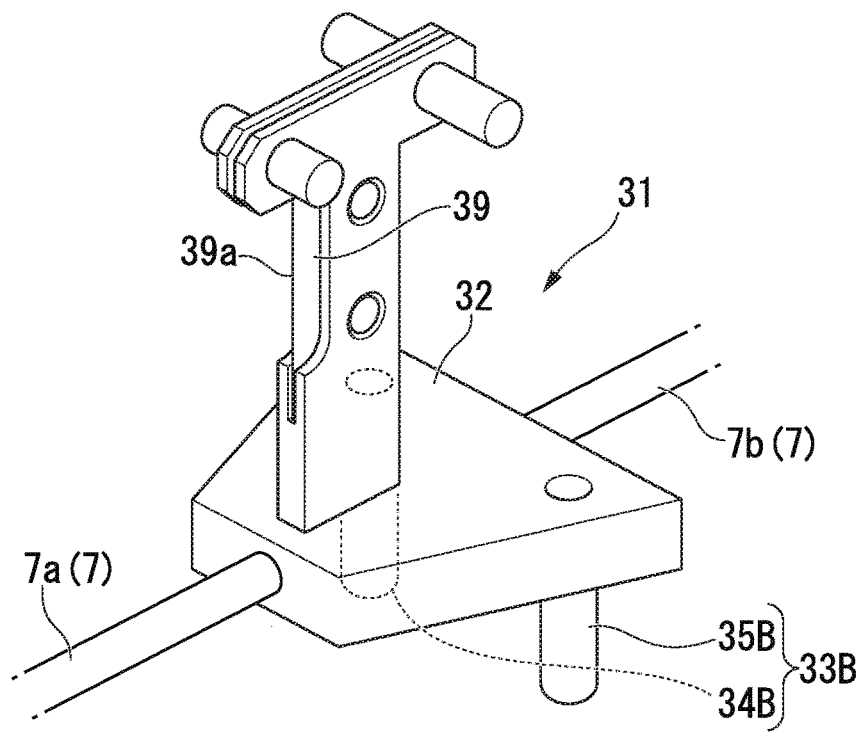
FIG. 20 is a view showing a modified example of the third embodiment of the present invention.
Figure 21:
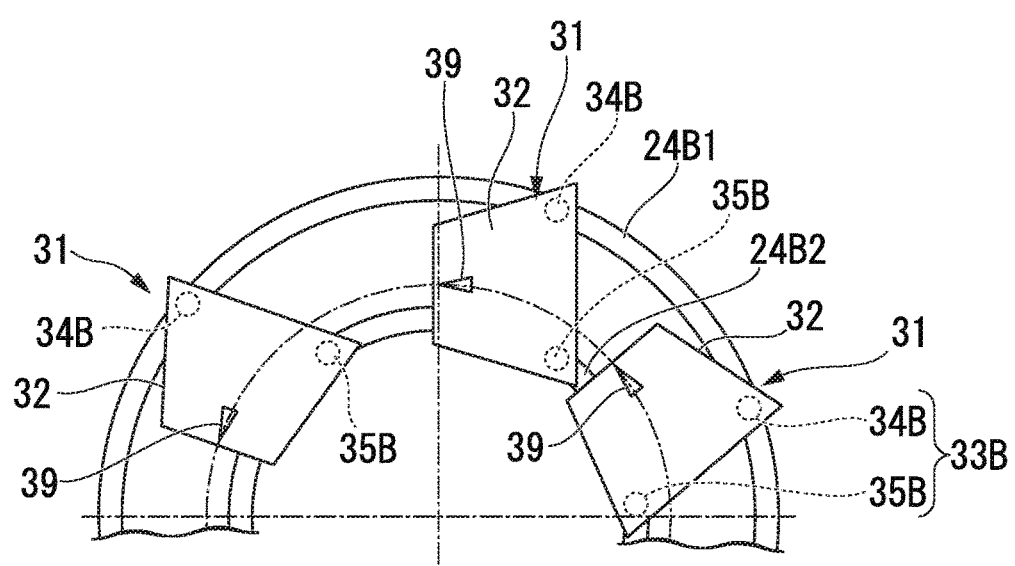
FIG. 21 is a view showing an action of a surgical instrument of the modified example of the third embodiment of the present invention.

An interval between the first guided section 34B and the second guided section 35B is changed with respect to an interval between the first guide groove 24B1 and the second guide groove 24B2, and thereby the direction of the blade section 39 is capable of being adjusted by changing the distance between the first guided section 34B and the second guided section 35B with respect to a distance between the first guide groove 24B1 and the second guide groove 24B2. For example, as shown in FIGS. 20 and 21, in a case that the blade section 39 is disposed at the distal side relative to first and second guided sections 34 and 35, a distance between the first guided section 34 and the second guided section 35 is made wider, compared to the example shown in FIG. 18. Thereby, a direction of a blade edge 39a of the blade section 39 is regulated by a tangential direction of the groove section 22 like the above embodiment.

While the embodiments of the present invention have been described with reference to the drawings, a specific constitution is not limited to these embodiments, and includes a change in design or the like without departing from the gist of the present invention.

For example, in the first embodiment, the constitution that four points consisting of the two points separated in the first guided section 34 and the two points separated in the second guided section 35 are in contact with the guide section 24 is shown, but each point may be independent. That is, instead of being provided with the first guided section 34 and the second guided section 35, four guided sections may be provided at positions separated from one another, and each of the four guided sections may be in contact with the guide section 24.

While the flexible surgical instrument 1 including the flexible tube 61 has been exemplarily described in the embodiments, a hard shaft may be provided instead of the flexible tube 61.

While an example in which the first jaw 10 and the second jaw 50 are opened and closed by using the open-close knob 66 has been described in the above-mentioned embodiments, the jaws may be configured such that an open-close operation in the cartridge unit 2 and dissection of the tissue by the blade section 39 of the actuation section 31 are performed as one operation. For example, when the actuation section 31 is moved to the distal side of the cartridge unit 2 by using the lever 67, the actuation section 31 may be configured to couple the first jaw 10 and the second jaw 50 to move the first jaw 10 toward the second jaw 50. In this case, the open-close operation in the cartridge unit 2 and dissection of the tissue by the blade section 39 of the actuation section 31 may be performed as one operation using the lever 67.

While embodiments of the present invention have been described, the technical scope of the present invention is not limited to the aforementioned embodiments. Without departing from the scope of the present invention, a combination of the components in the embodiments may be changed, or each component may be modified in various ways or be eliminated. The present invention is not limited by the aforementioned description.

What is claimed is:

1. A surgical instrument comprising:
an insertion section configured to be capable of inserting into a body;
a grasping member provided at a distal end portion of the insertion section and formed in a curved shape which is bent with respect to an longitudinal axis of the insertion section;
a guide section formed along the curved shape and disposed at the grasping member;
a first guided section having a disc shape which has an outer circumferential surface slidably contacting with the guide section;
a second guided section provided at a proximal side of the guide section closer than the first guided section and having a disc shape which has an outer circumferential surface slidably contacting with the guide section; and
a base to which the first guided section and the second guided section are attached;
a blade section fixed to the base and protrudes from the grasping member, the blade section being movably along the curved shape of the grasping member by sliding the first guided section and the second guided section along the guide section.

2. The surgical instrument according to claim 1, wherein the grasping member has a first jaw and a second jaw,
wherein the surgical instrument further comprising:
a bonding section configured to bond a tissue being grasped by the first and second jaws; and
a wire configured to extend from a proximal end portion of the guide section toward a distal end portion of the guide section, to be turned back at the distal end portion of the guide section, to extend toward the proximal end portion of the guide section, and to be coupled with the first guided section, and
wherein each of the outer circumferential surface of the first guided section and the outer circumferential surface of the second guided section have two contacting sections which are capable of contacting with the guide section.

3. The surgical instrument according to claim 2, wherein the first guided section is rotatable with respect to the base.

4. The surgical instrument according to claim 3, wherein the second guided section is rotatable with respect to the base.

5. The surgical instrument according to claim 1, wherein the guide section includes a first guide groove that is a groove formed along the curved shape of the grasping member, and a second guide groove that is formed in a bottom of the first guide groove and has a width narrower than the first guide groove, and
wherein the first guided section abuts on an inner surface of the first guide groove and is guided by the first guide groove, and
the second guided section abuts on an inner surface of the second guide groove and is guided by the first guide groove.

6. The surgical instrument according to claim 1, wherein the first guided section is rotatable with respect to the blade section.

* * * * *